United States Patent [19]

Drabek et al.

[11] Patent Number: 4,925,875
[45] Date of Patent: May 15, 1990

[54] N-BENZOYL-N'-2,5-DIHALO-4-PER-FLUOROALKOXYPHENYLUREAS, PESTICIDAL COMPOSITIONS CONTAINING THEM AND THEIR USE IN THE CONTROL OF PESTS

[75] Inventors: Jozef Drabek, Oberwil; Urs Siegrist, Eiken, both of Switzerland

[73] Assignee: Ciba-Geigy Corporation, Ardsley, N.Y.

[21] Appl. No.: 218,191

[22] Filed: Jul. 13, 1988

[30] Foreign Application Priority Data

Jul. 21, 1987 [CH] Switzerland .......................... 2751/88
May 20, 1988 [CH] Switzerland .......................... 1920/89

[51] Int. Cl.$^5$ ................... A01N 47/28; A01N 87/60; A01N 127/22
[52] U.S. Cl. ....................................... 514/594; 564/44; 564/442
[58] Field of Search ................... 564/442, 44; 514/594

[56] References Cited

U.S. PATENT DOCUMENTS 4,518,804  5/1985  Rigterink et al. .................. 564/442

FOREIGN PATENT DOCUMENTS 0071279  2/1983  European Pat. Off. .
0194688  9/1986  European Pat. Off. .
0226642  7/1987  European Pat. Off. .
0231152  8/1987  European Pat. Off. .
0235089  9/1987  European Pat. Off. .
253614  2/1987  Fed. Rep. of Germany .

*Primary Examiner*—Douglas W. Robinson
*Assistant Examiner*—Zohreh A. Fay
*Attorney, Agent, or Firm*—Kevin T. Mansfield; Edward McC. Roberts

[57] ABSTRACT

Novel substituted N-benzoyl-N'-2,5-dihalo-4-perfluoroalkoxyphenylureas of formula I

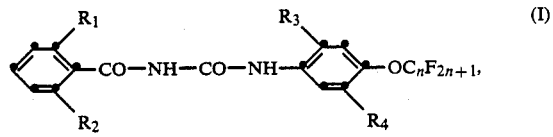

in which $R_1$ is hydrogen, fluorine, chlorine or bromine; $R_2$ is fluorine or chlorine; each of $R_3$ and $R_4$ is fluorine, chlorine or bromine; and n is 2, 3, 4, 5, 6, 7 or 8, processes and intermediates for their prepraration, their use in pest control, and pesticidal compositions that contain at least one compound of formula I as active ingredient, are disclosed. The preferred field of application is the control of pests in and on animals and plants.

7 Claims, No Drawings

N-BENZOYL-N'-2,5-DIHALO-4-PERFLUOROALK-OXYPHENYLUREAS, PESTICIDAL COMPOSITIONS CONTAINING THEM AND THEIR USE IN THE CONTROL OF PESTS

The present invention relates to novel substituted N-benzoyl-N'-2,5-dihalo-4-perfluoroalkoxy-phenylureas, processes and intermediates for their preparation and their use in pest control.

The compounds according to the invention have the formula I

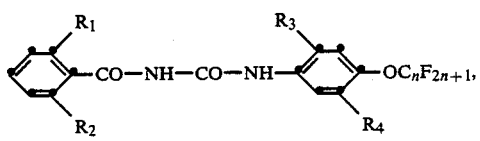

in which $R_1$ is hydrogen, fluorine, chlorine or bromine; $R_2$ is fluorine or chlorine; $R_3$ and $R_4$ are fluorine, chlorine or bromine; and n is 2, 3, 4, 5, 6, 7 or 8.

The perfluorinated $C_2-C_8$alkyl radicals suitable as substituents may be straight-chained or branched but are preferably unbranched. Suitable examples of such substituents are, inter alia, $CF_2CF_3$, $(CF_2)_2CF_3$, $(CF_2)_3CF_3$, $CF_2CF(CF_3)_2$ or the perfluoro-pentyl, -hexyl, -heptyl or -octyl radicals.

The compounds of formula I that should be given special emphasis are those in which $R_1$ is hydrogen, fluorine or chlorine; $R_2$ is fluorine or chlorine; $R_3$ is fluorine or chlorine; $R_4$ is fluorine, chlorine or bromine; and n is 2, 3, 4, 5, 6 or 7.

Compounds of formula I in which $R_1$ is hydrogen or fluorine; $R_2$ is fluorine or chlorine; each of $R_3$ and $R_4$ is chlorine; and n is 2, 3 or 4 are preferred.

The compounds according to the invention can be prepared according to processes that are known in principle. Such processes are described, inter alia, in DE-OS 21 23 236, 26 01 780 and 32 40 975. For example, the compounds of formula I can be obtained as follows:

(a) an aniline of formula II

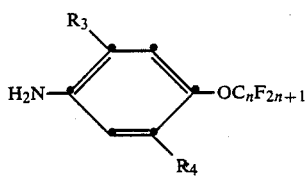

is reacted with a benzoyl isocyanate of formula III

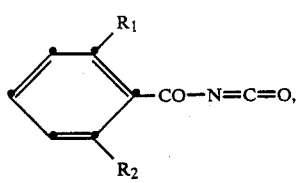

or
(b) an isocyanate of formula IV

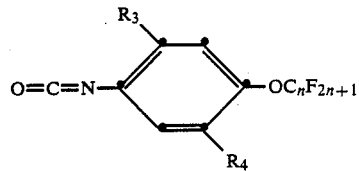

is reacted wtih a benzamide of formula V

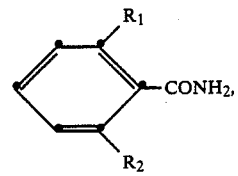

or
(c) an aniline of formula II is reacted with a urethane of formula VI

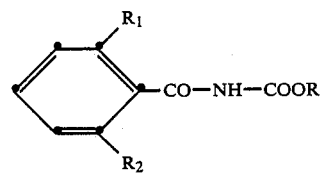

In the above formulae II to VI, the symbols $R_1$, $R_2$, $R_3$, $R_4$ and n have the meanings given for formula I and R is a $C_1-C_8$alkyl radical that may be unsubstituted or may be substituted by halogen, preferably chlorine.

The mentioned processes (a), (b) and (c) are preferably carried out under normal pressure and in the presence or an organic solvent or diluent. Suitable solvents and diluents are, for example, ethers and ethereal compounds, such as diethyl ether, dipropyl ether, dibutyl ether, dioxane, dimethoxyethane and tetrahydrofuran; N,N-dialkylated carboxylic acid amides; aliphatic, aromatic and halogenated hydrocarbons, especially benzene, toluene, xylene, chloroform, methylene chloride, carbon tetrachloride and chlorobenzene; nitriles, such as acetonitrile or propionitrile; dimethyl sulfoxide and ketones, for example acetone, methyl ethyl ketone, methyl isopropyl ketone and methyl isobutyl ketone. Process (a) is generally carried out at a temperature of from $-10°$ to $+200°$ C., preferably from $0°$ to $+100°$ C., for example at room temperature, in the absence or presence of an organic base, for example triethylamine. Process (b) is carried out at a temperature of from $0°$ to $+150°$ C., preferably at the boiling point of the solvent used, and in the absence or presence of an organic base, such as pyridine, and/or with the addition of an alkali metal or an alkaline earth metal, preferably sodium. For process (c), that is to say for the reaction of a urethane of formula VI with an aniline of formula II, temperatures of from approximately $+60°$ C. up to the boiling point of the reaction mixture are preferred, there being used as solvents especially aromatic hydrocarbons, such as toluene, xylenes, chlorobenzene, etc.

Some of the starting materials of formulae III, V and VI are known. Both the starting materials that are known and any that are novel can be prepared analogously to known processes.

The starting materials of formula II are novel compounds to which the present invention also relates. The compounds of formula II can be prepared in a manner known per se, for example by hydrogenating correspondingly substituted nitrobenzenes of formula VII

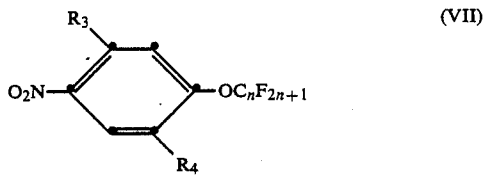

analogously to the process indicated in J. Org. Chem. 29 (1964), 1, (see also the literature cited in that reference). It is, however, also possible to obtain anilines of formula II by chemical reduction (for example by means of Sn(II) chloride/HCl) of the corresponding nitro compounds of formula VII (see Houben Weyl, "Methoden d. org. Chemie", 11/1, 422).

The nitro compounds of formula VII are also new and the present invention relates also to these. They can be prepared according to methods that are known in principle, for example by fluorination of compounds of formula VIII

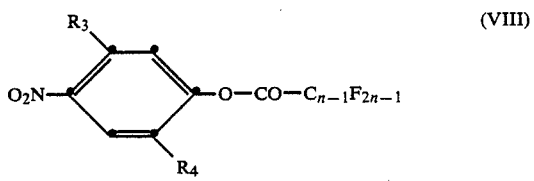

by means of $SF_4$ and HF (see, for example, Organic Reactions Vol. 21, pp. 37–42, 1974; Vol. 34, p. 339, 1985). The compounds of formula VIII are known or can be prepared according to methods that are known in principle.

It is possible to obtain benzoyl isocyanates according to formula III, for example as follows (see J. Agr. Food Chem. 21, 348 and 993; 1973):

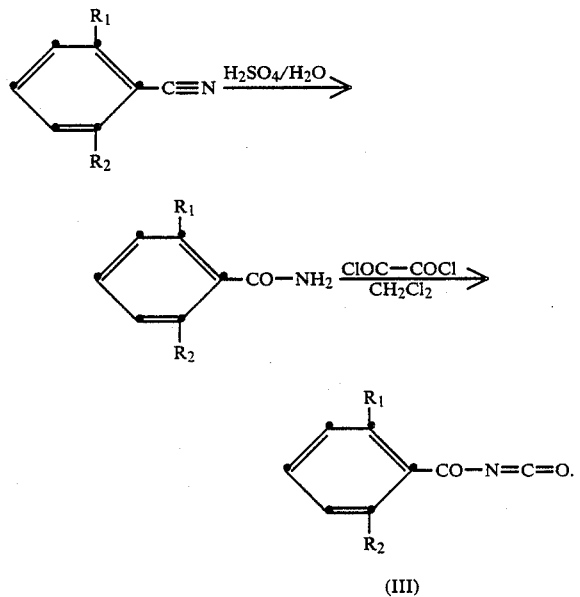

The 4-perfluoroalkoxyphenyl isocyanates of formula IV can be prepared, for example, by phosgenating the anilines of formula II by generally customary processes. The benzamides of formula V also to be used as starting materials are known (see, for example, Beilstein "Handbuch der organischen Chemie", Vol. 9, p. 336).

Urethanes of formula VI can be obtained according to methods that are known in principle by reacting a benzoyl isocyanate of formula III with a corresponding alcohol or by reacting a benzamide of formula V in the presence of a basic compound with a corresponding ester of the chloroformic acid Cl-COOR.

N-(2,6-dihalobenzoyl)-N'-(2,5-dichloro-4-haloalkoxyphenyl)-ureas having insecticidal action are known very generally from U.S. Pat. No. 4,518,804. Perfluorinated alkoxy radicals, however, are not disclosed.

Surprisingly, it has been found that the compounds according to the invention are valuable active ingredients in pest control, while being well tolerated by warm-blooded animals and by plants. The compounds of formula I are suitable, for example, for controlling pests in and on animals and plants. Such pests belong mainly to the strain of the arthropods, such as, especially, insects of the order Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera and arachnids of the order Acarina, such as, for example, mites and ticks. It is possible to control every stage of development of the pests, that is to say the adults, pupae and nymphs as well as, especially, the larvae and eggs. It is possible to control effectively especially the larvae and eggs of phytopathogenic insect and mite pests in ornamentals and useful plants, such as, for example, in fruit and vegetables, and especially in cotton. If the compounds of formula I are ingested by imagines, their action can manifest itself in the immediate death of the pests or in reduced oviposition and/or hatching rates. The latter phenomenon is to be observed especially in Coleoptera. In the control of pests that parasiticise animals, especially domestic animals and productive livestock, there come into consideration especially ectoparasites, such as, for example, mites and ticks and Diptera, such as, for example, *Lucilia sericata*. The compounds of formula I are also suitable for controlling snails in ornamentals and useful plants.

The good pesticidal activity of the compounds of formula I according to the invention corresponds to a mortality of at least from 50 to 60% of the mentioned pests.

The activity of the compounds of the invention or the compositions containing them can be substantially broadened and adapted to prevailing circumstances by the addition of other insecticides and/or acaricides. Additives that come into consideration are, for example, representatives of the following classes of active ingredients: organophosphorus compounds, nitrophenols and derivatives thereof, formamidines, ureas, carbamates, pyrethroids, chlorinated hydrocarbons and *Bacillus thuringiensis* preparations.

The compounds of formula I are used in unmodified form or, preferably, together with the adjuvants conventionally employed in the art of formulation, and are therefore formulated in known manner e.g. into emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I, or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil, or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of granulated materials of inorganic or organic nature can be used, e.g. especially dolomite or pulverised plant residues.

Depending on the nature of the compound of formula I to be formulated, or on the nature of the combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil. Mention may also be made of fatty acid methyltaurin salts and modified and unmodified phospholipids as surfactants.

More frequently, however, so called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in the art of formulation are described, inter alia, in the following publications:

"McCutcheon's Detergents and Emulsifiers Annual", MC Publishing Corp., Ridgewood, N.J., 1979;

Dr. Helmut Stache, "Tensid-Taschenbuch", Carl Hanser Verlag, Munich/Vienna 1981.

The pesticidal compositions usually contain 0.1 to 99%, preferably 0.1 to 95%, of a compound of formula I or combinations thereof with other insecticides or acaricides, 1 to 99.9% of a solid or liquid adjuvant, and 0 to 25%, preferably 0.1 to 20%, of a surfactant. Whereas commercial products will preferably be formulated as concentrates, the end user will normally employ dilute formulations containing considerably lower concentrations of active ingredient.

The compositions may also contain further auxiliaries such as stabilisers, antifoams, viscosity regulators, binders and tackifiers as well as fertilisers or other active ingredients in order to obtain special effects.

Example 1: Preparation

1.1. Intermediates

1.1.1. Nitrobenzenes

1.1.1.1. 2,5-dichloro-4-pentafluoroethoxynitrobenzene

An autoclave is charged with 20 g of 2,5-dichloro-4-nitrophenyl trifluoroacetate and evacuated. At from −10° to 0° C., first 60 g of hydrogen fluoride are added and then 14.3 g of sulfur tetrafluoride are introduced in portions with inert gas under pressure. The reaction mixture is then stirred for 15 hours at +50° C. The readily volatile portion is then distilled off at room temperature and the residue is taken up in methylene chloride and poured into ice-water. The organic phase is separated off and the aqueous phase is extracted twice with methylene chloride and, finally, the combined organic extracts are washed twice with water and twice with sodium carbonate and dried over sodium sulfate. The solvent is evaporated off and the residue is taken up in a hexane/ether mixture (30:1) and filtered over silica gel. After distilling off the solvent, the title compound of formula

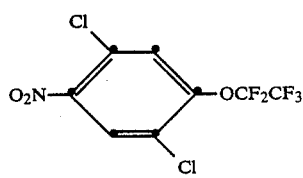
(Comp. 1.1.1.1.)

is obtained in the form of a pale yellow oil; $n_D^{22}$: 1.4678; b.p. 65°–68° C./0.1 torr.

The following compounds are prepared in an analogous manner:

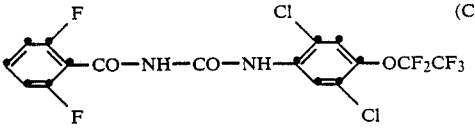

| Comp. No. | $R_3$ | $R_4$ | $C_nF_{2n+1}$ | phys. data |
|---|---|---|---|---|
| 1.1.1.2. | Cl | Cl | $(CF_2)_2CF_3$ | b.p. 74–77° C./0.15 torr |
| 1.1.1.3. | Cl | Cl | $(CF_2)_3CF_3$ | b.p. 76–82° C./0.05 torr |
| 1.1.1.4. | F | F | $(CF_2)_2CF_3$ | b.p. 55–58° C./0.05 torr |

1.1.2. Anilines

1.1.2.1. 2,5-dichloro-4-pentafluoroethoxyaniline 41 g of 2,5-dichloro-4-pentafluoroethoxynitrobenzene are dissolved in 410 ml of tetrahydrofuran and hydrogenated at room temperature for 32 hours in the presence of Raney nickel ($H_2$ absorption: 7.62 l). The reaction mixture is filtered and concentrated and the residue is distilled. The title compound of formula

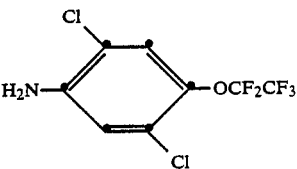
(Comp. 1.1.2.1.)

is obtained in the form of a colourless liquid; b.p. 56°–61° C./0.04 torr.

The following compounds are prepared in an analogous manner:

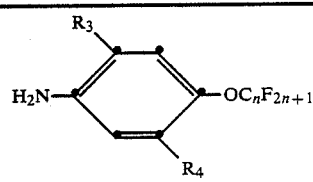

| Comp. No. | $R_3$ | $R_4$ | $C_nF_{2n+1}$ | phys. data |
|---|---|---|---|---|
| 1.1.2.2. | Cl | Cl | $(CF_2)_2CF_3$ | b.p. 110° C./0.04 torr |
| 1.1.2.3. | Cl | Cl | $(CF_2)_3CF_3$ | b.p. 140° C./0.08 torr |
| 1.1.2.4. | F | F | $(CF_2)_2CF_3$ | b.p. 95–100° C./0.04 torr |

1.2. End products

1.2.1. N-(2,6-difluorobenzoyl)-N'-(2,5-dichloro-4-pentafluoroethoxyphenyl)-urea 3.4 g of 2,6-difluorobenzoyl isocyanate, dissolved in 10 ml of dry toluene, are added at room temperature and with the exclusion of moisture to 5.6 g of 2,5-dichloro-4-pentafluoroethoxyaniline dissolved in 40 ml of dry toluene, and the batch is stirred for 10 hours. Approximately 60% of the solvent is then removed. The precipitate formed is filtered off with suction, washed with hexane and dried in vacuo. The title compound of formula (Comp. 1.2.1.)

is obtained in the form of colourless crystals; m.p. 178°–179° C.

The following compounds are prepared in an analogous manner:

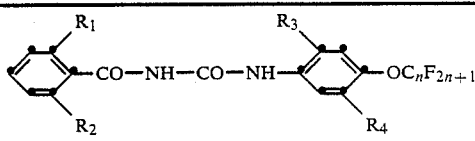

| Comp. No. | $R_1$ | $R_2$ | $R_3$ | $R_4$ | $C_nF_{2n+1}$ | phys. data |
|---|---|---|---|---|---|---|
| 1.2.2. | F | F | Cl | Cl | $(CF_2)_2CF_3$ | m.p. 176–178° C. |
| 1.2.3. | F | F | Cl | Cl | $(CF_2)_3CF_3$ | m.p. 171–173° C. |
| 1.2.4. | H | F | Cl | Cl | $CF_2CF_3$ | m.p. 164–165° C. |
| 1.2.5. | H | F | Cl | Cl | $(CF_2)_3CF_3$ | m.p. 162–164° C. |
| 1.2.6. | H | Cl | Cl | Cl | $CF_2CF_3$ | m.p. 177–179° C. |
| 1.2.7. | H | Cl | Cl | Cl | $(CF_2)_2CF_3$ | m.p. 178–179° C. |
| 1.2.8. | H | Cl | Cl | Cl | $(CF_2)_3CF_3$ | m.p. 166–168° C. |
| 1.2.9. | F | F | F | F | $(CF_2)_2CF_3$ | m.p. 191–193° C. |

-continued

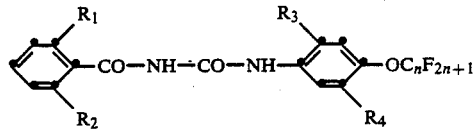

| Comp. No. | $R_1$ | $R_2$ | $R_3$ | $R_4$ | $C_nF_{2n+1}$ | phys. data |
|---|---|---|---|---|---|---|
| 1.2.10. | H | Cl | F | F | $(CF_2)_2CF_3$ | m.p. 168–169° C. |
| 1.2.11. | H | F | F | F | $(CF_2)_2CF_3$ | m.p. 163–164° C. |
| 1.2.12. | Cl | Cl | F | F | $(CF_2)_2CF_3$ | m.p. 212–213° C. |
| 1.2.13. | Cl | F | F | F | $(CF_2)_2CF_3$ | m.p. 218–222° C. |
| | F | F | Cl | Cl | $(CF_2)_4CF_3$ | |
| | F | F | Cl | Cl | $(CF_2)_6CF_3$ | |
| | F | F | Cl | Cl | $(CF_2)_7CF_3$ | |
| | F | F | F | Br | $(CF_2)_2CF_3$ | |
| | F | F | F | Br | $(CF_2)_6CF_3$ | |
| | F | F | F | F | $(CF_2)_6CF_3$ | |
| | H | Cl | Cl | Cl | $(CF_2)_4CF_3$ | |
| | H | Cl | Cl | Cl | $(CF_2)_6CF_3$ | |
| | H | Cl | Cl | Cl | $(CF_2)_7CF_3$ | |

Example 2: Formulations for compounds of formula I according to Preparation Example 1.2. (throughout percentages are by weight)

| 2. Emulsifiable concentrates | |
|---|---|
| compound according to Preparation Example 1.2. | 10% |
| castor oil polyethylene glycol ether (36 moles of ethylene oxide) | 25% |
| butanol | 15% |
| ethyl acetate | 50% |

Emulsions of any desired concentration can be produced from such concentrates by dilution with water.

| 2.2 Solutions | (a) | (b) |
|---|---|---|
| compound according to Preparation Example 1.2. | 10% | 5% |
| polyethylene glycol (mol. wt. 400) | 70% | — |
| N-methyl-2-pyrrolidone | 20% | 20% |
| epoxidised coconut oil | — | 1% |
| petroleum fraction (boiling range 160–190° C.) | — | 74% |

These solutions are suitable for application in the form of microdrops.

| 2.3. Granulates | (a) | (b) |
|---|---|---|
| compound according to Preparation Example 1.2. | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier and the solvent is subsequently evaporated off in vacuo.

| 2.4. Extruder granulate | |
|---|---|
| compound according to Preparation Example 1.2. | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| 2.5. Coated granulate | |
|---|---|
| compound according to Preparation Example 1.2. | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.6. Dusts | (a) | (b) | (c) | (d) |
|---|---|---|---|---|
| compound according to Preparation Example 1.2. | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by intimately mixing the carriers with the active ingredient and optionally grinding the mixture in a suitable mill.

| 2.7. Wettable powders | (a) | (b) | (c) |
|---|---|---|---|
| compound according to Preparation Example 1.2. | 20% | 50% | 75% |
| sodium lignosulfonate | 5% | 5% | — |
| sodium lauryl sulfate | 3% | — | 5% |
| sodium diisobutyl naphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 67% | 27% | — |

The active ingredient is thoroughly mixed with the adjuvants and the mixture is ground in a suitable mill, affording wettable powders which can be diluted with water to give suspensions of any desired concentration.

| 2.8. Suspension concentrate | |
|---|---|
| compound according to Preparation Example 1.2. | 40% |
| ethylene glycol | 10% |
| nonylphenolpolyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

Example 3: Biological tests 3.1. Action against *Musca domestica*

A sugar cube is so moistened with a solution of the test compound that the concentration of active ingredient in the cube after drying is 500 ppm. The treated cube is placed on a dish together with a wet cotton wool swab and covered with a beaker. 10 adult one-week-old, OP-resistant flies are placed under the beaker and kept at 25° C. and 50% humidity. The insecticidal action is determined after 24 hours by evaluating the mortality rate.

Compounds according to Example 1.2. exhibit good activity in the above test.

3.2. Action against *Lucilia sericata*

1 ml of an aqueous formulation containing 0.5% of test compound is added at 50° C. to 9 ml of a culture medium. Then about 30 freshly hatched Lucilia sericata larvae are added to the culture medium, and the insecticidal action is determined after 48 and 96 hours by evaluating the mortality rate.

In this test, compounds according to Example 1.2. exhibit good activity against Lucilia sericata.

3.3. Action against *Aedes aegypti*

A concentration of 12.5 ppm is obtained by pipetting a specific amount of a 0.1% solution of the test compound in acetone onto the surface of 150 ml of water in a container. After the acetone has evaporated, 30 to 40 two-day-old Aëdes larvae are put into the container. Mortality counts are made after 2 and 7 days.

Compounds according to Example 1.2. exhibit good activity in this test.

3.4. Insecticidal stomach poison action

Cotton plants (about 20 cm high) are sprayed with an aqueous emulsion (obtained from a 10% emulsifiable concentrate) that contains the test compound in a concentration of 100 ppm.

After the coating has dried, each of the cotton plants is populated with Spodoptera littoralis and Heliothis virescens larvae in the $L_3$ stage. The test is carried out at 24° C. and 60% relative humidity. The mortality and defects in the development and sloughing of the larvae are determined at 24-hour intervals.

Compounds according to Example 1.2. exhibit good activity in this test.

3.5. Action against *Spodoptera littoralis* and *Heliothis virescens* (larvae and eggs)

Three cotton plants about 15–20 cm high grown in pots are treated with a sprayable liquid formulation of the test compound. After the spray-coating has dried, the potted plants are placed in a sheet-metal container that has a capacity of about 20 liters and is covered with a glass plate. The humidity inside the covered container is so regulated that no condensation water is formed. No direct light is allowed to fall on the plants. The three plants are then infested with a total of:

(a) 50 larvae of *Spodoptera littoralis* or *Heliothis virescens* in the $L_1$ stage;
(b) 20 larvae of *Spodoptera littoralis* or *Heliothis virescens* in the $L_3$ stage;
(c) two egg deposits of *Spodoptera littoralis* or *Heliothis virescens* (for that purpose, in each case 2 leaves of a plant are enclosed in a plexiglass cylinder closed at both ends with gauze); two egg deposits of Spodoptera or a portion of a cotton leaf on which eggs of Heliothis have been deposited are(is) added to the enclosed leaves.

After 4 and 5 days, an evaluation is made in comparison with untreated controls taking into account the following criteria:

(a) number of surviving larvae,
(b) inhibition of larval development and sloughing,
(c) feeding damage (skeletonising damage and pitting damage),
(d) hatching rate (number of larvae that have hatched from the eggs).

Compounds according to Example 1.2., in a concentration of 400 ppm, exhibit good overall activity in the above test.

3.6. Ovicidal action against *Spodoptera littoralis*

Eggs of *Spodoptera littoralis* deposited on filter paper are cut out of the paper and immersed in a 0.05% by weight solution of the test compound in a mixture of acetone and water (1:1). The treated egg deposits are then removed from the mixture and stored at 28° C. and 60% relative humidity in plastic dishes.

After 5 days, the hatching rate, that is to say the number of larvae that have developed from the treated eggs, is determined.

Compounds according to Example 1.2. exhibit good activity in the above test.

3.7. Action against *Laspeyresia pomonella* (eggs)

Egg deposits of Laspeyresia pomonella not more than 24 hours old are immersed for 1 minute, on filter paper, in an aqueous acetonic solution containing 400 ppm of the test compound. When the filter paper has dried it is placed, with the eggs, in a petri dish and left at a temperature of 28° C. After 6 days the percentage hatching rate from the treated eggs is evaluated.

Compounds according to Example 1.2. exhibit good activity in the above test.

3.8. Influence on the reproduction of *Anthonomus grandis*

Anthonomus grandis adults which are not more than 24 hours old after hatching are transferred in groups of 25 beetles to barred cages. The cages populated with the beetles are then immersed for 5 to 10 seconds in an acetonic solution containing 0.1% by weight of the test compound. When the beetles are dry again they are placed in covered dishes containing feed and are left for copulation and oviposition. Egg deposits are flushed out with running water twice to three times weekly, counted, disinfected by putting them for 2 to 3 hours in an aqueous disinfectant, and then placed in dishes containing a suitable larval diet. A count is made after 7 days to determine whether larvae have developed from the deposited eggs.

In order to determine the duration of the reproduction-influencing effect of the test compounds, the egg deposits of the beetles are monitored over a period of about four weeks. Evaluation is made by assessing the reduction in the number of deposited eggs and larvae hatched from them in comparison with untreated controls.

Compounds according to Example 1.2. exhibit a good reproduction-reducing activity in the above test.

3.9. Action against *Anthonomus grandis* (adults)

Two cotton plants in the 6-leaf stage, in pots, are each sprayed with wettable aqueous emulsion formulations containing 100 ppm of the test compound. After the spray-coating has dried (about 1.5 hours) each plant is populated with 10 adult beetles (*Anthonomus grandis*). Plastic cylinders, covered at the top with gauze, are then slipped over the treated plants populated with the test insects to prevent the beetles from migrating from the plants. The treated planted are kept at 25° C. and about 60% relative humidity. Evaluation is made after 2, 3, 4 and 5 days to determine the percentage mortality of the beetles (percentage in dorsal position) and the anti-feeding action as compared with untreated controls.

Compounds according to Example 1.2. exhibit good activity in this test.

3.10. Action against *Epilachna varivestis*

*Phaseolus vulgaris* plants (dwarf beans) about 15–20 cm in height are sprayed with aqueous emulsion formulations of the test compound in a concentration of 800 ppm. After the spray-coating has dried, each plant is populated with 5 larvae of *Epilachna varivestis* (Mexican bean beetle) in the $L_4$ stage. A plastic cylinder is slipped over the infested plants and covered with a copper gauze top. The test is carried out at 28° C. and 60% relative humidity.

The percentage mortality is determined after 2 and 3 days. Evaluation of any feeding damage (anti-feeding effect), and of defects in development and sloughing, is made by observing the test insects for a further 3 days.

Compounds according to Example 1.2. exhibit good activity in the above test.

3.11. Ovicidal action against *Heliothis virescens* and *Spodoptera littoralis*

Corresponding amounts of a wettable powder formulation containing 25% by weight of the test compound are mixed with sufficient water to produce an aqueous emulsion with an active ingredient concentration of 400 ppm.

One-day-old egg deposits of Heliothis on cellophane and of Spodoptera on paper are immersed in these emulsions for 3 minutes and then collected by suction on round filters. The treated deposits are placed in petri dishes and kept in the dark at 28° C. and 60% relative humidity. The hatching rate, i.e. the number of larvae which have developed from the treated eggs, in comparison with untreated controls, is determined after 5 to 8 days.

In the above test, compounds according to Example 1.2. exhibit an 80 to 100% ovicidal action (mortality) against Heliothis virescens and Spodoptera littoralis.

3.12. Stomach-poison action against *Heliothis virescens* larvae ($L_1$)

Potted soybean plants in the 4- to 5-leaf stage are sprayed with an aqueous emulsion (obtained from a 10% emulsifiable concentrate) containing the test compound in a concentration of 0.8 ppm.

After the spray-coating has dried, each soybean plant is populated with 20 *Heliothis virescens* larvae in the $L_1$ stage. The test is carried out at 26° C. and about 55% relative humidity. An assessment is made 6 days after populating the plants, the mortality of the larvae being determined as a percentage.

| Compounds | Percentage mortality at 0.8 ppm |
|---|---|
| 1. Comp. No. 1.2.1. | 70 |
| 2. Comp. No. 1.2.2. | 85 |
| 3. Comp. No. 1.2.3. | 100 |
| 4. Comp. Example 1B | 25 |

| Compounds | Percentage mortality at 0.8 ppm |
|---|---|
| U.S. Pat. No. 4,518,804* | |

*F-C₆H₂(F)(F)-CO-NH-CO-NH-C₆H₂(Cl)(Cl)-OCF₂CHF₂*

We claim:
1. A compound of the formula

$$\begin{array}{c} R_1 \\ \phantom{x} \\ R_2 \end{array}\!\!-\!\!CO-NH-CO-NH-\!\!\begin{array}{c} R_3 \\ \phantom{x} \\ R_4 \end{array}\!\!-OC_nF_{2n+1},\quad (I)$$

in which
$R_1$ is hydrogen, fluorine, chlorine or bromine;
$R_2$ is fluorine or chlorine;
$R_3$ and $R_4$ is each chlorine; and
n is 2, 3 or 4.

2. A compound of claim 1, in which n is 2 or 4.
3. A compound of claim 1 of the formula F-C₆H₂(F)-CO-NH-CO-NH-C₆H₂(Cl)(Cl)-OCF₂CF₃, F-C₆H₂(F)-CO-NH-CO-NH-C₆H₂(Cl)(Cl)-O(CF₂)₂CF₃, F-C₆H₂(F)-CO-NH-CO-NH-C₆H₂(Cl)(Cl)-O(CF₂)₃CF₃, F-C₆H₃-CO-NH-CO-NH-C₆H₂(Cl)(Cl)-OCF₂CF₃, F-C₆H₃-CO-NH-CO-NH-C₆H₂(Cl)(Cl)-O(CF₂)₃CF₃, Cl-C₆H₃-CO-NH-CO-NH-C₆H₂(Cl)(Cl)-OCF₂CF₃, C₆H₄-CO-NH-CO-NH-C₆H₂(Cl)(Cl)-O(CF₂)₂CF₃, -continued

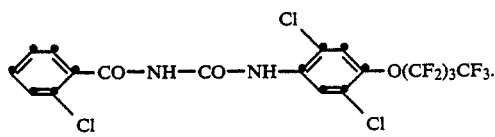

4. A pesticidal composition containing as active component a pesticidally effective amount of at least one compound of formula I

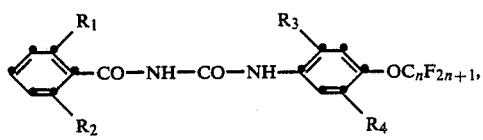

in which $R_1$ is hydrogen, fluorine, chlorine or bromine; $R_2$ is fluorine or chlorine; $R_3$ and $R_4$ is chlorine and n is 2, 3 or 4 together with suitable carriers and/or adjuvants.

5. A method of controlling pests on animals and plants, which comprises contacting the pests, in their various stages of development, with a compound of formula I

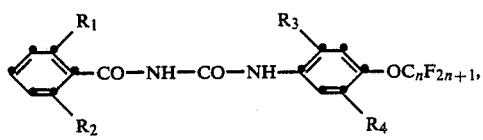

in which $R_1$ is hydrogen, fluorine, chlorine or bromine; $R_2$ is fluorine or chlorine; $R_3$ and $R_4$ are chlorine; and n is 2, 3 or 4.

6. A method of controlling pests according to claim 5 wherein the pests are insects and arachnids.

7. A method of controlling pests according to claim 6 wherein the pests are larval stages of plant-destructive insects.

* * * * *